United States Patent [19]
Bobrove et al.

[11] Patent Number: 5,962,505
[45] Date of Patent: Oct. 5, 1999

[54] METHOD FOR TREATING HOT FLASHES IN HUMANS

[76] Inventors: Arthur M. Bobrove, 1539 Walnut Dr.; Jeffrey D. Urman, 1880 Hamilton Ave., both of Palo Alto, Calif. 94030

[21] Appl. No.: 09/184,512

[22] Filed: Nov. 2, 1998

Related U.S. Application Data

[60] Provisional application No. 60/098,629, Aug. 31, 1998.
[51] Int. Cl.$^6$ ..................... A61K 31/40
[52] U.S. Cl. ........................ 514/424
[58] Field of Search .............. 514/424

[56] References Cited

U.S. PATENT DOCUMENTS

| | | | |
|---|---|---|---|
| 4,096,254 | 6/1978 | Benson et al. | 424/242 |
| 5,155,045 | 10/1992 | Cutler et al. | 436/65 |
| 5,462,950 | 10/1995 | Fontana | 514/324 |
| 5,744,463 | 4/1998 | Bair | 514/177 |

FOREIGN PATENT DOCUMENTS

| | | |
|---|---|---|
| 1102345 | 6/1981 | Canada . |

OTHER PUBLICATIONS

Atkin and Brown, (1996) "Treatment of Diabetic Gustatory Sweating with Topical Glycopyrrolate Cream" *Diabetic Medicine* 13:493–494.

Hays, (1978) "The Frey Syndrome: A Review and Double Blind Evaluation of the Topical Use of a New Anticholinergic Agent" *The Laryngoscope* 88:1796–1824.

Hays et al., (1982) "The Frey Syndrome: A Simple Effective Treatment" *Otolaryngol Head Neck Surg* 90:419–425.

Goldberg et al., (1994) "Transdermal Clonidine for Ameliorating Tamoxifen–induced Hot Flashes" *J. Clin. Onc.* 12:155–158.

Loprinzi et al., (1994) "Megestrol Acetate for the Prevention of Hot Flashes" *N. Engl. J. Med.* 331:347–351.

May and McGuirt, (1989) "Frey's Syndrome: Treatment with Topical Glycopyrrolate" *Head & Neck* 11:85–89.

Shaw et al., (1997) "A Randomised Controlled Trial of Topical Glycopyrrolate, the First Specific Treatment for Diabetic Gustatory Sweating" *Diabetologia* 40:299–301.

Stegehuis and Ellis, (1989) "Treatment of Frey's Syndrome (Gustatory Sweating) with Topical Glycopyrrolate: Case Report" *NZ Med J.* 103(875):479.

Merck Index, Ninth Edition, Merck & Co., Rahway, NJ, p. 583, #4337 (1976).

*Primary Examiner*—Raymond Henley, III
*Attorney, Agent, or Firm*—Burns, Doane, Swecker & Mathis, LLP

[57] ABSTRACT

This invention is directed to methods for treating hot flashes as a consequence of declining levels of estrogen or androgen in humans. Specifically, the methods of this invention involve the topical administration of glycopyrrolate compounds to humans.

8 Claims, No Drawings

METHOD FOR TREATING HOT FLASHES IN HUMANS

CROSS-REFERENCE TO RELATED APPLICATIONS

This application claims priority to provisional U.S. Patent Application No. 60/098,629 filed Aug. 31, 1998, which is incorporated herein in its entirety.

BACKGROUND OF THE INVENTION

1. Field of the Invention

This invention is directed to methods for treating hot flashes as a consequence of declining estrogen levels or androgen levels in humans. Specifically, the methods of this invention involve the topical administration of an effective amount of a glycopyrrolate compound to a human suffering from hot flashes.

REFERENCES

The following publications, patent applications and patents are cited in this application as superscript numbers:
1. Loprinzi et al., "Megestrol acetate for the prevention of hot flashes" *N. Engl. J. Med.* 331:347–351 (1994)
2. Goldberg et al., "Transdermal clonidine for ameliorating tamoxifen-induced hot flashes" *J. Clin. Onc.* 12:155–158 (1994)
3. Hays et al., "The Frey syndrome: a simple, effective treatment" *Otolaryngol Head Neck Surg.* 90:419–425 (1982)
4. Atkin et al., "Treatment of diabetic gustatory sweating with topical glycopyrrolate cream" *Diabetic Medicine* 13:493–494 (1996)
5. Shaw et al., "A randomized controlled trial of topical glycopyrrolate, the first specific treatment for diabetic gustatory sweating" *Diabetologia* 40:299–301 (1997)
6. May et al., "Frey's Syndrome: Treatment with topical glycopyrrolate" *Head & Neck* (January/Febuary 1989) p.85–89
7. Col. Leonard L. Hays, "The Frey syndrome: A review and double blind evaluation of the topical use of a new anticholinergic agent" *The Laryngoscope* 88:1976 (1978)
8. *Remington's Pharmaceutical Sciences,* Mace Publishing Company Philadelphia Pa. $_{17}$th ed. (1985)
9. U.S. Pat. No. 5,525,347, Kellner et al.
10. U.S. Pat. No. 2,956,062, Lunsford et al.

All of the above publications, patent applications and patents are herein incorporated by reference in their entirety to the same extent as if each individual publication, patent application or patent was specifically and individually indicated to be incorporated by reference in its entirety.

STATE OF THE ART

Hot flashes or flushing occur commonly in menopausal women. This is characterized by a sudden onset of warmth in the face and neck and often progressing to the chest. Such an episode generally lasts several minutes and is evidenced by a visible flushing of the skin. Often such episodes are accompanied by sweating, dizziness, nausea, palpitations and diaphoresis. Such symptoms can disrupt sleep and interfere with the quality of life. Although the cause of hot flashes are not completely understood, they are thought to be a disorder of thermoregulation within the hypothalamus that is a consequence of declining estrogen levels. Thus it is not surprising that hot flashes also occur in a high percentage of women taking the anti-estrogen drug tamoxifen.

Men may also have hot flashes following androgen-deprivation therapy (from bilateral orchiectomy or treatment with a gonadotrophin-releasing-hormone agonist) for metastatic prostate cancer.

Although estrogen replacement therapy is the most direct and effective treatment for hot flashes in women, there are women in whom such therapy is contraindicated, i.e. women with breast cancer or a strong family history of breast cancer, a history of clotting, severe migraine, or who are averse to taking the drug.

In these women, there are alternative medications to prevent or treat the serious consequences of menopause, such as osteoporosis and raised serum lipid levels. Included in this category are the selective estrogen-receptor modulators (SERMs), such as raloxifene, which selectively bind to and activate the estrogen receptors of some tissues such as bone, and block the receptors of others, i.e. breast and uterus. In so doing, they lack the negative impact that prolonged estrogen therapy may have on these organs. However, in contrast to estrogen, SERMs do not prevent hot flashes.

Other than estrogen-replacement therapy, there are no effective means to alleviate hot flashes. Low dose oral megestrol acetate, a progestational agent, was shown to reduce the frequency of hot flashes in both men and women in a short term study[1]. However, chronic adrenal insufficiency can be a side effect of low dose megestrol acetate when taken long term. Transdermal clonidine, a centrally active α-agonist, had only a moderate effect on the frequency and severity of hot flashes in tamoxifen-treated women[2]. Accordingly, there is a need for a method of treating hot flashes.

Topical glycopyrrolate has been used previously to treat gustatory sweating associated with diabetic autonomic neuropathy[4,5]. In this disorder, sweating that often is profuse, begins soon after the patient ingests food, starting on the forehead and then involving the face, scalp and neck. A solution of glycopyrrolate was applied to the face of the patient which prevented the gustatory sweating.

Similarly, glycopyrrolate has also been used previously to treat gustatory sweating associated with Frey's syndrome which may develop after parotidectomy[3,6,7]. Frey's syndrome is believed to result from the aberrant reinnervation of the sweat glands of the face by the severed parotid parasympthetic nerve fibers.

In both diabetic gustatory sweating and Frey's syndrome, the profuse facial sweating is induced by the specific stimulus of eating. Moreover, the sweating in each is a consequence of a distinct neuropathological process. In contrast, the hot flashes of menopause occur spontaneously without a specific stimulus and are the consequence of a normal or physiological process, the natural decline in circulating levels of estrogen.

This invention is directed in part to the discovery that the transdermal application of a glycopyrrolate compound to a human overcomes many of the prior problems in treating hot flashes and the perspiration associated therewith. Additionally, it provides advantages heretofore not achieved by conventional treatments for the hot flashes associated with low levels of estrogen and/or androgen. For example, the glycopyrrolate compound to be applied does not have the side effects associated with estrogen replacement therapy. Secondly, the glycopyrrolate compound can be applied to both males and females.

SUMMARY OF THE INVENTION

This invention is directed to methods for treating hot flashes by the topical application of an effective amount of a glycopyrrolate compound to a human.

This invention is directed to a method for alleviating the hot flashes in a human, which method comprises the steps of identifying a human susceptible to hot flashes; and administering to said human a therapeutically effective amount of a glycopyrrolate compound.

This invention is also directed to a method for alleviating hot flashes in a human, which method comprises the steps of identifying a human susceptible to hot flashes; and administering to said human a therapeutically effective amount of a pharmaceutical composition comprising a pharmaceutically acceptable excipient and a glycopyrrolate compound.

DETAILED DESCRIPTION OF THE PREFERRED EMBODIMENTS

This invention is directed to methods for treating hot flashes by the topical application of a glycopyrrolate compound to a human.

Definitions

As used herein, the following terms have the following meanings;

The term "glycopyrrolate compound" means a compound of the formula:

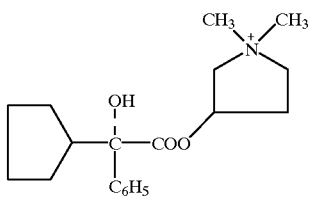

wherein $X^-$ is a pharmaceutically acceptable counter ion salt.

The term "glycopyrrolate compound" also refers to analogues of glycopyrrolate capable of inhibiting hot flashes wherein the chemical structure has been modified so as to introduce, modify and/or remove one or more functionalities of the structure. For example, such modification can result in the removal of an OH functionality, the introduction of an amine functionality, the introduction of a halo functionality, and the like. In so far as the glycopyrrolate analogues are capable of inhibiting hot flashes as a consequence of low levels of estrogen and androgen, they are encompassed by the definition of "glycopyrrolate compound".

The term "therapeutically effective amount" means that amount of a drug or pharmaceutical agent that will elicit the biological or medical response of a tissue, system, animal or human that is being sought by a researcher, veterinarian, medical doctor or their clinician. In particular, with regard to treating the disorders of hot flashes and perspiration associated therewith, the "therapeutically effective amount" is intended to mean that amount of the glycopyrrolate compound that will prevent or alleviate the hot flashes. Hot flashes are a condition commonly known and understood by the average consumer who lacks any medical skill.

The glycopyrrolate compound is effective over a wide dosage range and is generally administered in a therapeutically effective amount. It will be understood, however, that the amount of the compound actually administered may be determined by a physician in light of the relevant circumstances, including the condition to be treated, the chosen route of administration, the actual compound administered and its relative activity, the age, weight, and response of the individual patient, the severity of the patient's symptoms, and the like.

The compound is preferably administered topically. The daily dose of the compounds may vary depending on the medical condition of the patient, the skin status, and the age of the patient. Compounds of the present invention may be administered in a single daily dose, or the total daily dose may be administered in divided doses of two, three or four times daily. The compound may be applied to the face, scalp, neck, trunk, back, limbs, axillae and/or groin of the human. Preferably, the glycopyrrolate compound is applied to the face, neck or scalp of the human.

Patients susceptible to hot flashes and perspiration associated therewith include, but are not limited to, women undergoing menopause, either natural or surgical; patients taking selective estrogen-receptor modulators (SERMs); patients taking tamoxifen; and male patients undergoing androgen deprivation therapy.

The term "pharmaceutically acceptable counter salt" refers to salts which retain the biological effectiveness and properties of the glycopyrrolate compounds of this invention, which are not biologically or otherwise undesirable, and which carry an anionic charge. The glycopyrrolate compounds of this invention form salts by virtue of the presence of the quarternary ammonium thereon.

Pharmaceutically acceptable counter salts may be prepared from inorganic and organic acids. Salts derived from inorganic acids include hydrochloric acid, hydrobromic acid, hydrogen fluoride, hydrogen iodide, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The compounds of the present invention may be administered in a pharmaceutical composition comprising the active compound in combination with a pharmaceutically acceptable carrier adapted for topical administration. Topical pharmaceutical compositions may be in the form of a solution, cream, ointment, mousse, gel, lotion, powder or aerosol formulation adapted for application to the skin. These topical pharmaceutical compositions containing the compounds of the present invention ordinarily include from about 0.05% to 5.0% by weight of the active compound, more preferably from about 0.5% to 2.5% by weight of the active compound, in admixture with a pharmaceutically acceptable excipient.

Topical preparation containing the active compound can be admixed with a variety of carrier materials or pharmaceutically acceptable excipients well known in the art. When the excipient serves as a diluent, it can be a solid, semi-solid, or liquid, which acts as a vehicle, carrier or medium for the active ingredient. Thus, the compositions can be in the form of powders, suspensions, emulsions, solutions, syrups, alcoholic solutions, ointments, topical cleansers, cleansing creams, skin gels, skin lotions, mousses, roll-ons, aerosol or non-aerosol sprays in cream or gel formulations and soft gelatin capsules.

The compounds of the present invention may be administered in the form of liposome delivery systems, such as small unilamellar vesicles, large unilamellar vesicles and multilamellar vesicles. Liposomes can be formed from a variety of phospholipids, such a cholesterol, stearylamine or phosphatidylcholines.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include alcohols, aloe vera gel, allantoin, glycerin, vitamin A and E oils, mineral oil, PPG2, myristyl propionate lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The glycopyrrolate composition may additionally contain one or more optional additives such as colorants, perfumes, etc. In practice, each of these optional additives should be both miscible and compatible with the glycopyrrolate compound. Compatible additives are those that do not prevent the use of the glycopyrrolate compound in the manner described herein.

Other suitable formulations for use in the present invention can be found in *Remington's Pharmaceutical Sciences*[6].

Methods

The methods of this invention comprise the application of a glycopyrrolate compound to the skin surface of a human, which glycopyrrolate compound acts to inhibit hot flashes and the perspiration associated therewith.

The skin surface is preferably dried, and then a glycopyrrolate compound is applied to the skin surface of the human at the desired site. The compound can be applied to the face, scalp, neck, trunk, back, limbs, axillae and/or groin of the human. Preferably, the glycopyrrolate compound is applied to the face of the human, in particular the cheeks, neck and forehead, taking care to avonose a eyes, nose and mouth.

Sufficient amounts of the composition are employed to cover (i.e., coat) the entire skin surface with a layer of the glycopyrrolate compound. If necessary, excess glycopyrrolate compound can be removed from the skin with a wipe or tissue paper.

After application, the glycopyrrolate compound penetrates the skin very slowly and has been associated with few side effects[3,4,5]. The glycopyrrolate is allowed to dry. Cosmetics can be applied over the glycopyrrolate.

Compositions

Glycopyrrolate is readily commercially available. Glycopyrrolate can be made as follows. α-phenylcyclopentaneglycolic acid is esterified by refluxing with methanol in the presence of hydrochloric acid and the resulting ester is transesterified with 1-methyl-3-pyrrolidinol using sodium as a catalyst. The transester is then reacted with methyl bromide to give glycopyrrolate[9,10].

Utility

It has been found that the application of glycopyrrolate to the skin of humans suffering from hot flashes as a consequence of reduced levels of estrogen and androgen, reduces or eliminates the incidence of unwanted hot flashes and perspiration.

EXAMPLES

Example 1

The patient is a 56 year old women with a history of hot flashes and perspiration associated with menopause. She complained about profuse facial, scalp and anterior neck sweating that occurred randomly with the hot flashes.

As a treatment, the patient was offered and consented to the application of 0.5 % glycopyrrolate topical lotion, which she applied once daily to her forehead and face, sparing her mouth and eyes.

The lotion consisted of 1.5 gm glycopyrrolate; 75 ml ethanol; 2.4 gm hydroxyethylcell; brought to a total volume of 300 ml with water and the pH adjusted to 2–4.5.

This treatment resulted in complete resolution of the perspiration associated with the hot flashes. Daily topical application of the glycopyrrolate roll-on lotion has continued to alleviate her symptoms during the subsequent 6 months that she has used this treatment.

The patient also reported that the application of the glycopyrrolate lotion also alleviated the hot flashes she was experiencing associated with menopause.

Example 2

A 51 year old woman treated with tamoxifen for breast cancer described 8 months of hot flashes and perspiration that awakened her from sleep.

Daily application of 0.5% glycopyrrolate in a "roll on" solution to her face greatly relieved her symptoms and resulted secondarily in improvement in the quality of her sleep.

Example 3

A 48 year old woman treated with tamoxifen for breast cancer described hot flashes and perspiration beginning on her scalp, which interfered with her sleep.

Daily application of 0.5% glycopyrrolate in a "roll on" solution to her scalp and around her hair line greatly relieved her symptoms and resulted in improved sleep.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

We claim:

1. A method for alleviating hot flashes in a human, which method comprises:

a) identifying a human susceptible to hot flashes; and b) administering to said human a therapeutically effective amount of a glycopyrrolate compound such that the hot flashes are substantially reduced.

2. The method according to claim 1, wherein the glycopyrrolate compound is applied to the skin of the human.

3. The method according to claim 2, wherein the glycopyrrolate compound is applied to the face and neck of the human.

4. The method according to claim 2, wherein the glycopyrrolate compound is applied to the scalp of the human.

5. The method according to claim 1, wherein the glycopyrrolate compound has formula I:

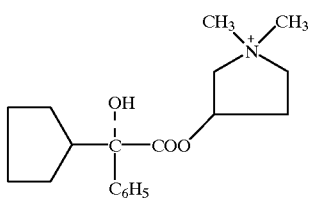

wherein X⁻ is a pharmaceutically acceptable counter ion salt.

6. A method for alleviating hot flashes in a human, which method comprises:
   a) identifying a human susceptible to hot flashes; and
   b) administering to said human a therapeutically effective amount of a pharmaceutical composition comprising a pharmaceutically acceptable excipient and a glycopyrrolate compound.

7. The method according to claim 6, wherein the glycopyrrolate compound has formula I:

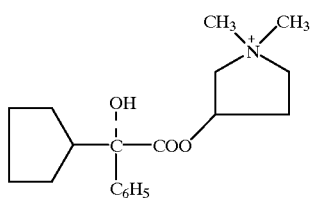

wherein X⁻ is a pharmaceutically acceptable counter ion salt.

8. The method according to claim 6 wherein the concentration of glycopyrrolate compound in the pharmaceutical composition is from 0.05% to 5.0% by weight.

* * * * *